United States Patent
Dozol et al.

(10) Patent No.: US 6,630,114 B1
(45) Date of Patent: Oct. 7, 2003

(54) CALIXARENE DERIVATIVES, PREPARATION METHOD AND USE OF SAID DERIVATIVES TO EXTRACT ANTINIDES AND LATHANIDES

(75) Inventors: Jean-François Dozol, Pierreuert (FR); Hélène Rouquette, Manosque (FR); Alejandro Garcia Carrera, Provence (FR); Laetitia Delmau, Marseille (FR); Volker Böhmer, Mainz (DE); Alexander Shivanyuk, Fin (FI); Christian Muzigmann, Münster (DE)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/869,961

(22) PCT Filed: Jan. 17, 2000

(86) PCT No.: PCT/FR00/00085

§ 371 (c)(1),
(2), (4) Date: Jul. 10, 2001

(87) PCT Pub. No.: WO00/42051

PCT Pub. Date: Jul. 20, 2000

(30) Foreign Application Priority Data

Jan. 18, 1999 (FR) .............................................. 99 00442

(51) Int. Cl.[7] .......................... C22B 60/00; C07F 9/50; C07F 9/53
(52) U.S. Cl. ........................... 423/9; 423/10; 423/21.5; 549/220; 549/221
(58) Field of Search ................................. 549/200, 218, 549/220, 221; 423/9, 10, 21.5

(56) References Cited

U.S. PATENT DOCUMENTS

| | | | | |
|---|---|---|---|---|
| 3,243,254 A | * | 3/1966 | Paciello et al. ................. | 423/9 |
| 5,607,591 A | | 3/1997 | Dozol et al. | |
| 5,622,821 A | * | 4/1997 | Selvin et al. ................... | 435/6 |
| 5,717,126 A | * | 2/1998 | Paciello et al. ................ | 558/78 |
| 5,866,087 A | | 2/1999 | Dozol et al. | |
| 5,926,687 A | | 7/1999 | Dozol et al. | |
| 6,306,355 B1 | | 10/2001 | Delmau et al. | |
| 6,312,653 B1 | | 11/2001 | Delmau et al. | |

FOREIGN PATENT DOCUMENTS

| | | |
|---|---|---|
| WO | WO 94/12502 | 6/1994 |
| WO | WO 94/24138 | 10/1994 |
| WO | WO 96/23800 | 8/1996 |

OTHER PUBLICATIONS

K. B. Yatsimirskii, et al., Chemical Abstract, vol. 090, No. 23, Jun. 4, 1979, AN 185911, "Proton NMR Study of Phosphonyl–Containing Macrocyclic Polyesters Using Lanthanide Shift Reagents", 1979.

A. Arduini, et al., J. Org. Chem., vol. 60, No. 5, pp. 1454–1457, "Calix[4]arenes Blocked in a Rigid Cone Conformation by Selective Functionalization at the Lower Rim", 1995.

A. Arduini, et al., Tetrahedron, vol. 52, No. 16, pp. 6011–6018, "New Calix[4]arenes Having Electron Donating Groups at the Upper Rim as Molecular Platforms and Host Molecules", 1996.

* cited by examiner

Primary Examiner—Jean F. Vollano
(74) Attorney, Agent, or Firm—Oblon, Spivak, McClelland, Maier & Neustadt, P.C.

(57) ABSTRACT

The invention relates to new calixarenes according to the formula:

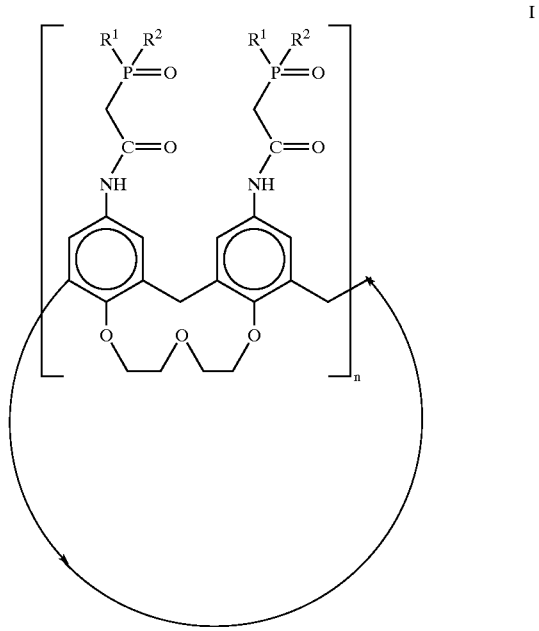

wherein $R^1$ and $R^2$, which may be identical or different, are alkyl, alkoxy or aryl groups, and n is an integer equal to 2, 3 or 4.

Said calixarenes may be used to extract actinides and lanthanides from aqueous solutions.

14 Claims, 4 Drawing Sheets

CALIXARENE DERIVATIVES, PREPARATION METHOD AND USE OF SAID DERIVATIVES TO EXTRACT ANTINIDES AND LATHANIDES

FIELD OF THE INVENTION

The present invention relates to new calixarene derivatives and the preparation method and use of said derivatives to extract actinides and lanthanides.

More specifically, it relates to calixarenes comprising a phosphinoxide-acetamide substituent, offering beneficial properties for the extraction of actinides and lanthanides, particularly trivalent actinides and lanthanides.

Therefore, said new calixarenes may be used to extract actinides and lanthanides present in aqueous solutions such as aqueous effluents from used nuclear fuel reprocessing installations or used nuclear fuel dissolution solutions.

STATE OF THE RELATED ART

The use of macrocyclic ligands such as calixarenes comprising a phosphinoxide-acetamide substituent, to extract metals such as lanthanides and actinides from aqueous solutions has already been envisaged, as disclosed in WO-A-96/23800 [1].

In said derivatives, the phosphinoxide-acetamide substituent is arranged directly on the phenyl cycles of the calixarene and said phenyl cycles are also substituted by alkoxy groups, for example of 5 to 18 carbon atoms.

Calix[4]arenes-bis-rings comprising two ether-ring links between two opposed benzene cores 1 and 3, and 2 and 4 are also known from the document FR-A-2 698 362 [2]. Said substances are particularly useful for the selective extraction of cesium.

Although the efficiency of said calixarenes in the extraction of actinides and lanthanides or caesium is satisfactory, research was continued to improve the performances of calixarenes in the extraction of trivalent actinides and lanthanides.

DESCRIPTION OF THE INVENTION

The present invention relates to new calixarene derivatives comprising a phosphinoxide-acetamide substituent which offer improved performances in relation to the calixarenes described in documents [1] and [2].

According to the invention, the calixarene complies with the formula:

I wherein $R^1$ and $R^2$, which may be identical or different, are alkyl, alkoxy or aryl groups, and n is an integer equal to 2, 3 or 4.

In this calixarene, the presence of ether-oxide links between adjacent benzene cores makes the structure of the calixarene rigid and more efficient in the extraction of trivalent actinides and lanthanides.

In formula I given above, $R^1$ and $R^2$ may be alkyl, alkoxy or aryl groups. The alkyl and alkoxy groups may be linear or ramified, preferentially comprising 1 to 18 carbon atoms. The aryl groups that may be used for $R^1$ and $R^2$ are monovalent groups derived from an aromatic or heterocyclic core by removing a hydrogen atom from one of the carbon atoms of the cycle. Examples of such groups include phenyl, naphthyl, pyridyl, thiophenyl and substituted phenyl groups.

Preferentially, $R^1$ and $R^2$ each represent a phenyl group or an alkoxy, for example ethoxy, group, where $R^1$ represents the phenyl group and $R^2$ represents an alkoxy, for example ethoxy, group.

The calixarenes according to the invention may comprise 4 to 8 phenyl cycles. Preferentially, the calixarene comprises 4 phenyl cycles (n=2).

The calixarenes according to formula I according to the invention may be prepared using a method comprising the following steps:

a) nitration of a calixarene according to the formula:

II wherein R³ represents an alkyl group and n is as defined above, to obtain the nitro derivative according to the formula:

III b) reduction of the nitro derivative according to formula III into an amino derivative according to the formula:

IV c) reaction of the amino derivative according to formula IV with a phosphinoxide acetate according to the formula:

V wherein R¹ and R² are as defined above, and R⁴ represents the p-nitrophenyl or 2,4 dinitrophenyl group.

The phosphinoxideacetate according to formula V used in the final step may be prepared using alkyl phosphinite corresponding to the formula:

where R¹ and R² have the correspondences given above and R⁵ is an alkyl group comprising 1 to 4 carbons, by reacting said group with ethyl bromoacetate, followed by hydrolysis and esterification of the acid obtained with nitrophenol or dinitrophenol.

According to an alternative embodiment, the calixarenes according to formula I wherein R¹ and/or R² are an alkoxy group, may be prepared using a method comprising the following steps:

a) nitration of a calixarene according to the formula:

II wherein R³ represents an alkyl group and n is as defined above, to obtain the nitro derivative according to the formula:

III b) reduction of the nitro derivative according to formula III into an amino derivative according to the formula:

c) reaction of the amino derivative according to formula IV with bromoactyl chloride according to the formula:

VI to obtain the calixarene derivative according to the formula:

d) reaction of the derivative according to formula VII with a phosphonate or phosphinate according to the formula:

VIII wherein $R^1$ is an alkyl, alkoxy or aryl group and $R^2$ is an alkoxy group.

The calixarenes according to formula I of the invention may be used to separate at least one metal selected from actinides and lanthanides present in an aqueous solution, such as dissolution solutions and aqueous effluents from used nuclear fuel reprocessing installations.

The aqueous solution may be a nitric solution containing 1 to 4 mol/l of $HNO_3$.

To carry out this separation, the aqueous solution containing the metal(s) to be separated is placed in contact with a non-miscible phase comprising at least one calixarene complying with formula I given above, to extract the metal(s) in the non-miscible phase.

Said non-miscible phase is generally composed of a solution of the calixarene(s) according to the invention in a suitable organic solvent.

Examples of solvents that may be used include alkyl benzenes and nitrophenyl alkyl ethers.

Preferentially, an ether such as ortho-nitrophenyl hexyl ether is used as the solvent.

The calixarene concentration of the non-miscible liquid phase particularly depends on the solvent used. Concentrations ranging from $5.10^{-5}$ to $10^{-3}$ mol/l, for example a $10^{-3}$ mol/l concentration, may be used.

To implement the separation method according to the invention, the aqueous solution may be placed in contact with said non-miscible liquid phase in conventional liquid-liquid extraction installations such as mixers-clarifiers, centrifugal extractors, pulsating columns, etc., but also by means of supported liquid membranes.

The supported membrane technique consists of immobilising the non-miscible liquid phase on a solid substrate such as polypropylene. Using this technique, it is possible to transfer the metals to be separated from the aqueous solution in which they are contained into an aqueous re-extraction solution. In this case, one of the sides of the membrane is in contact with the first aqueous solution containing the metals to be separated and the other side is in contact with an aqueous re-extraction solution.

The substrate of the supported liquid membrane may be a microporous membrane wherein the pores are filled with calixarene in solution in a suitable organic solvent. Said microporous membrane may be made of polypropylene, polyvinylidene fluoride or polytetrafluorethylene. Said membrane may be used as a separation between a first compartment with the aqueous solution containing the metals to be separated and a second compartment with the aqueous re-extraction solution.

To obtain satisfactory extraction with supported liquid membranes, it is advantageous to use thin, highly porous membranes with a small pore diameter. Said membranes may be used in the form of modules such as plane membrane or hollow fibre ultra- or microfiltration modules, used to process high fluid flow rates.

After the extraction of the metal(s) to be separated in the non-miscible liquid phase, they may be recovered by re-extraction in an aqueous re-extraction solution. Said solution may be an aqueous complexing agent solution. The complexing agent may be an organic acid or an organic acid salt such as methylene diphosphonic acid, oxalic acid, citric acid, oxalates and citrates. The use of such solutions makes it possible to obtain the re-extraction of separated metals with high yields.

The invention's other characteristics and advantages will be seen more clearly on reading the following examples, which are naturally given as an illustration and are not exhaustive, with reference to the appended figures.

BRIEF DESCRIPTION OF THE FIGURES

FIG. 1 (1A and 1B) is a diagram representing the synthesis of calixarenes according to formula I according to a first embodiment of the invention.

FIG. 2 (2A and 2B) is a diagram representing the synthesis of calixarenes according to formula I according to a second embodiment of the invention.

DETAILED DESCRIPTION OF EMBODIMENTS

Examples 1 to 3 illustrate the preparation of calixarenes complying with formula I given above, where $R^1$ and $R^2$ represent the phenyl group Ph (example 1), $R^1$ represents the ethoxy group and $R^2$ represents the phenyl group (example 2) and $R^1$ and $R^2$ represent the ethoxy group (example 3).

EXAMPLE 1

Preparation of Tetrakis(3-diphenyl-phosphinoxide-acetamide-)-bis-ring-3-calix[4]arene (Compound 1)

Figure 1A:
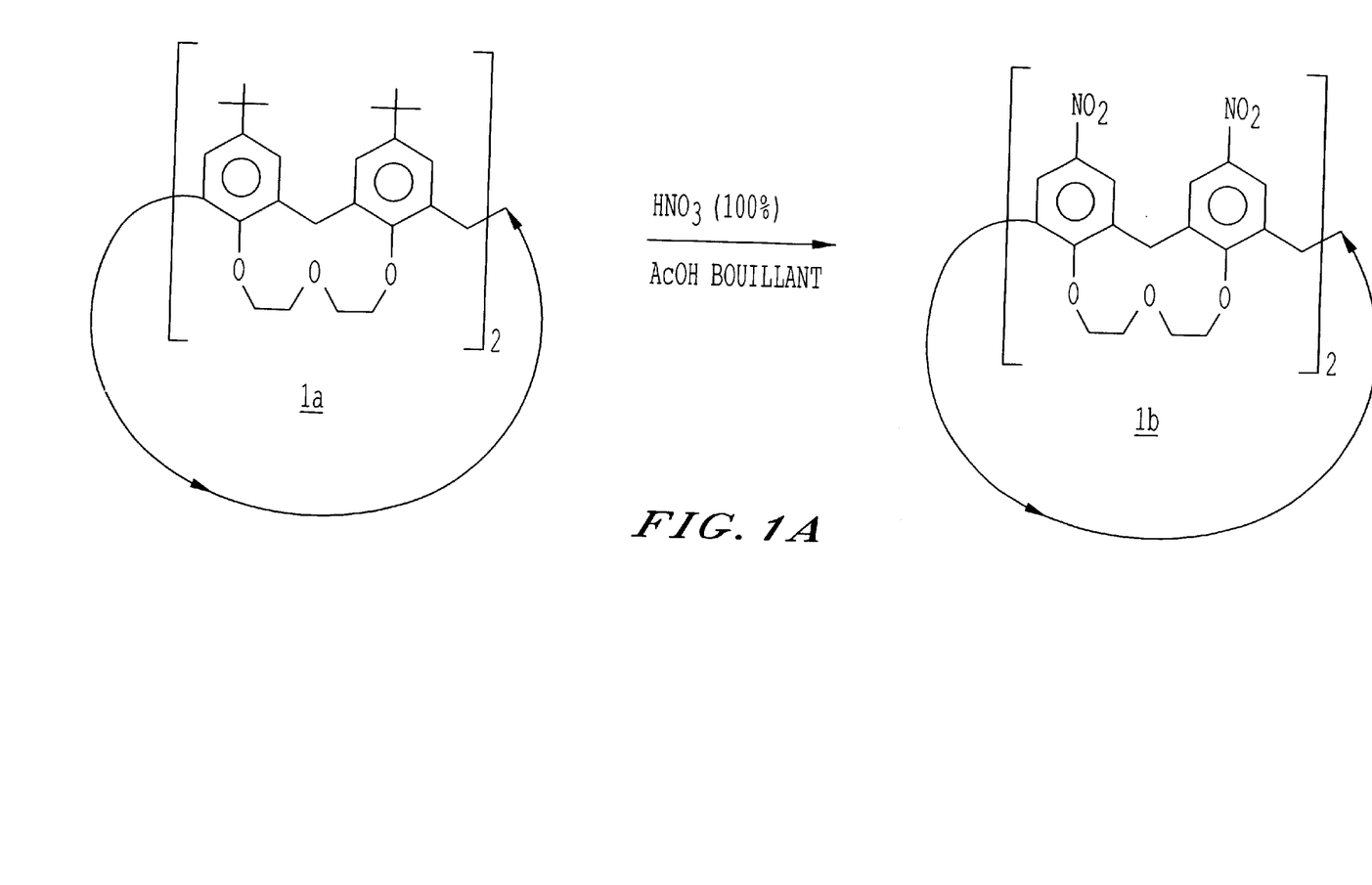
Figure 1B:
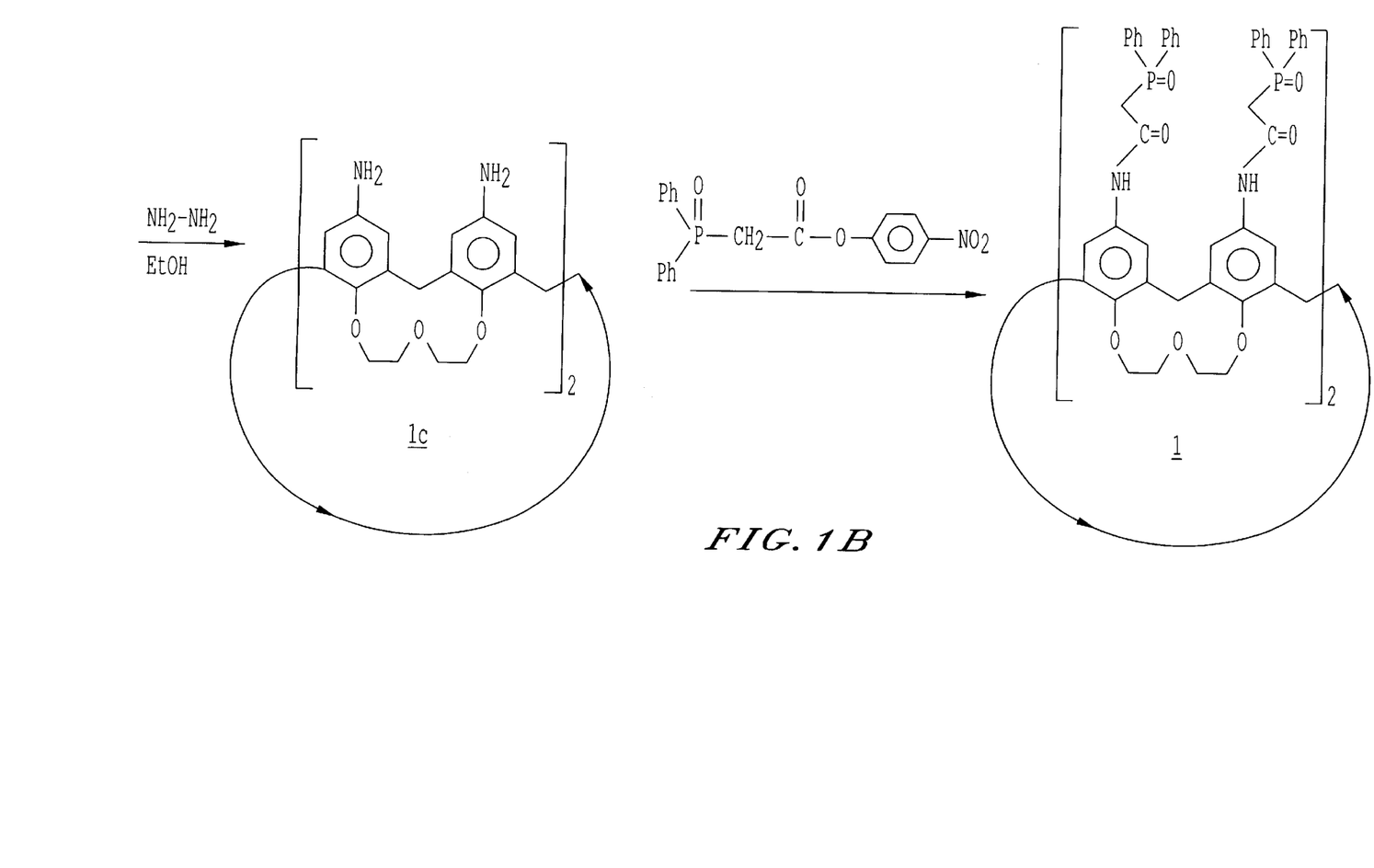

For this synthesis, the reaction diagram represented in FIG. 1 is followed, starting with compound 1a, tetrakis-tert-butyl-bis-ring-3-calix[4]-arene, which was prepared as described by A. Arduini et al in J. Org. Chem., 1995, 60, p. 1454–1457 [3].

a) Preparation of Nitrated Derivative of bis-Ring-3-calix[4]arene (Compound 1b)

0.2 g of calixarene 1a is dissolved in 7 ml of glacial acetic acid by heating to approximately 100° C. 5 to 7 ml of 100% $HNO_3$ is added to this solution once. The reaction takes place immediately and a colourless precipitate is formed in 3 to 5 minutes.

After 10 to 20 minutes of stirring, the precipitate of compound 1b is separated by filtration and is washed with glacial acetic acid (2×5 ml), followed by methanol (5 ml), and dried in a vacuum.

In order to eliminate the traces of acetic acid, the compound 1b is dissolved in a mixture of ethanol and toluene and the solution is evaporated in a vacuum.

This operation is repeated 3 times and the colourless solid product is then dried in an advanced vacuum at 60° C., for 2 hours. The compound 1b is thus obtained with a 40% yield.

The nuclear magnetic resonance spectrum of this compound complies with that given by Arduini et al, Tétrahédron, 1996, 52, p. 6011–6018 [4].

b) Preparation of Tetrakis-amino-bis-ring-3-calix[4]-arene (Compound 1c)

5 ml of hydrazine $N_2H_4$, $H_2O$ is added once to a suspension of 0.3 g of compound 1b and 0.3 g of Raney nickel in 30 ml of ethanol. Before use, the Raney nickel was washed with ethanol.

The mixture is reflux-boiled for 8 hours by periodically adding $N_2H_4$, $H_2O$ (5 ml every two hours). After approximately 3 hours, the suspension is completely dissolved. The reaction mixture is evaporated in a vacuum and the residue is dissolved in 10 ml of an ethanol:toluene mixture (1:1) and the solution obtained is evaporated in a vacuum to eliminate water. This operation is repeated 3 times and the residue is dissolved in ethanol and precipitated with hexane. The compound 1c is obtained with a 95% yield.

The nuclear magnetic resonance spectrum data for this compound complies with that given in the reference [3] mentioned above.

c) Preparation of Compound 1

To a suspension of 0.2 g (0.32 mmol) of compound 1c in 20 ml of dry toluene, 3 ml of triethyl amine was added at once, followed by 0.7 g (1.8 mmol) of the active ester p-nitrophenyl(di-phenyl-phosphoryl) acetate). The reaction mixture is placed under vigorous stirring at ambient temperature for 5 hours. During this operation, the reaction mixture becomes yellow and after 3 hours, a precipitate similar to oil of a yellowish colour is formed. After 8 hours of stirring, 80 ml of $CH_2Cl_2$ of reaction mixture is added to dissolve the precipitate. The solution is washed with 1M NaOH (3×50 ml), so that the aqueous layer is colourless, and then with demineralised water (2×50 ml). The solution is evaporated in a vacuum. The product obtained is dissolved in an ethanol-toluene mixture and evaporated in a vacuum to eliminate water. The crystalline product obtained is dissolved in $CH_2Cl_2$ and reprecipitated twice with hexane. Finally, the colourless product obtained is dried in a high vacuum, at 60° C., for 4 hours, to eliminate the rest of the solvents.

Compound 1 is obtained with a 62% yield, the characteristics of this compound are as follows:

Melting point: 211–213° C.;

$^1$H NMR (400 MHz, DMSO-$d_6$) δ 9.77 (s, 4H), 7.85–7.75 (m, 16H), 7.60–7.46 (m, 24H), 7.07 (s large, 4H), 7.02 (s large, 4H), 4.88 (d, J=12.2 Hz, 2H), 4.35 (d, J=11.8 Hz, 2H), 4.22–4.07 (m, 12H), 3.68 (d, J=14.0 Hz, 8H), 3.60–3.51 (m, 4H), 3.09 (d, J=11.5 Hz, 2H), 3.01 (d, J=11.8 Hz, 2H).

FD-MS m/z 1593.6 (23%) [M' 1593.6].

EXAMPLE 2

Preparation of Tetrakis(3-phenyl-ethyl-phosphinate-acetamide)-bis-ring-3-calix[4]arene (Compound 2)

Figure 2A:
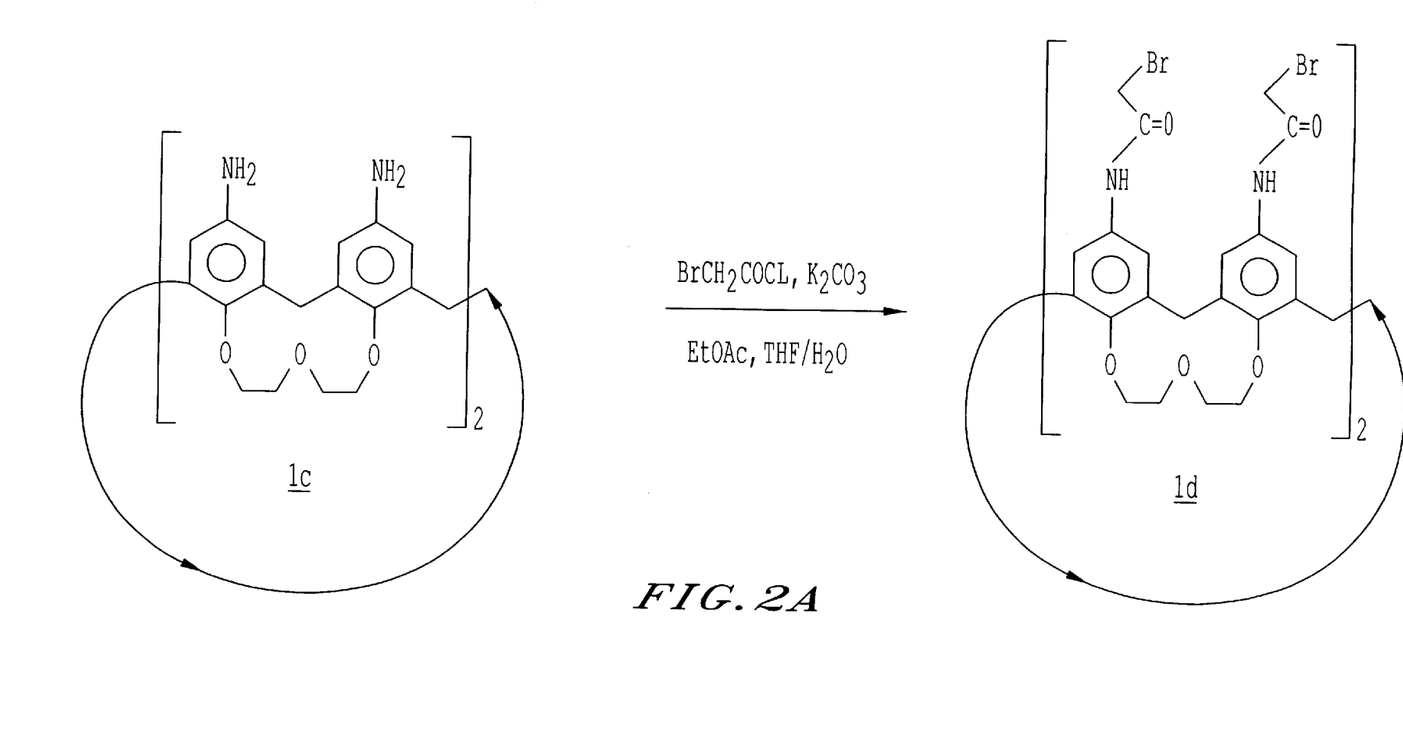
Figure 2B:
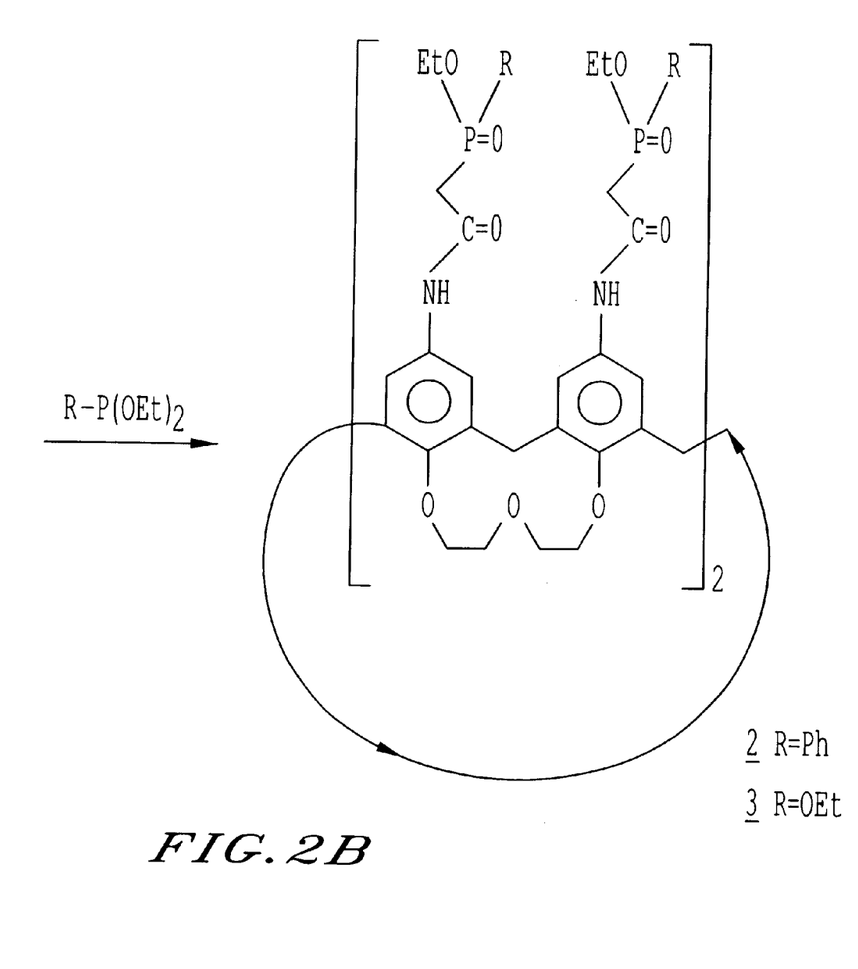

For this preparation, the reaction diagram represented in FIG. 2 is followed starting with the tetra-amino compound 1c obtained in example 1.

a) Preparation of Tetrakis-bromo Acetamide-bis-ring-3-calix[4]arene (Compound 1d)

To a solution of 0.4 g of the tetra-amino compound 1c in a mixture of 5 ml of tetrahydrofuran THF and 10 ml of ethyl acetate, 20 ml of a 1 M aqueous solution of $K_2CO_3$ is added. 3 times 6 ml of bromoacetyl chloride is added under vigorous stirring. The stirring of the reaction mixture is continued for 2 hours at ambient temperature, and 50 ml of ethyl acetate is then added and the two layers formed are separated. The organic layer is washed with water (3×50 ml) and then dried on $Na_2SO_4$ and evaporated in a vacuum. The compound 1d is obtained in the form of a colourless solid with an 86% yield.

The characteristics of compound 1d are as follows:

Melting point: 249–251° C.;

$^1$H NMR (400 MHz, CDCl$_3$ DMSO-$d_6$ 10:1) δ: 9.47 (s, 4H), 7.05 (s large, 4H), 7.03 (s large, 4H), 4.79 (d, J=12.0 Hz, 2H), 4.22 (d, J=12.0 Hz, 2H), 4.10–3.40 (m, 16H), 3.00 (d, J=12.0 Hz, 2H), 2.95 (d, J=12.0 Hz, 2H).

b) Preparation of Tetrakis(3-ethyl-phenyl-phosphinate-acetamide)-bis-ring-3-calix[4]arene (Compound 2)

To a solution of 0.2 g of tetra-bromoacetamide 1d in 10 ml of THF, 10 ml of ethyl phenylphosphinate PhP(OEt)$_2$ is added, and the reaction mixture is placed under stirring at 70° C. for 64 hours in a nitrogen atmosphere. The reaction medium is poured into 100 ml of hexane. The precipitate formed is separated by filtration and washed with hexane. It is reprecipitated twice in a THF-hexane mixture, which gives the analytically pure compound 2 in the form of a colourless solid with a 58% yield.

The characteristics of compound 2 are as follows:

Melting point: 157–162° C.;

$^1$H NMR (400 MHz, DMSO $d_6$) δ: 9.75–9.68 (m, 4H), 7.85–7.42 (m, 20H), 7.10, 7.05, 7.00 (3s large, 8H), 4.91 (d large, J=12.5 Hz, 2H), 4.36 (d large, J=11.3 Hz, 2H), 4.25–4.08 (m, 12H), 4.05–3.93 (m, 4H), 3.92–3.81 (m, 4H), 3.63–3.53 (m, 4H), 3.26–3.16 (m, 8H), 3.11 (d large, J=11.3 Hz, 2H), 3.04 (d large, J=11.3 Hz, 2H), 1.23–1.15 (m, 12H);

FD-MS m/z 1465.2 (18%) [M$^+$ 1465.4].

EXAMPLE 3

Preparation of Tetrakis(diethylphosphonate-acetamide)bis-ring-3 calix[4]arene (Compound 3)

To prepare this compound, the tetrabromoacetamide derivative 1d obtained in example 2 is used.

A solution of 0.2 g of tetrabromoacetamide 1d in 10 ml of P(OEt)$_3$ is placed under stirring at 70° C. for 64 hours in a nitrogen atmosphere. The solution is poured into 50 ml of hexane under stirring. The colourless precipitate formed is separated by filtration and washed with hexane. The unprocessed product containing P(OEt)$_3$ is additionally purified by reprecipitation using a CH$_2$Cl$_2$ solution using hexane. Compound 3 is obtained in the form of a colourless solid with a 67% yield.

The characteristics of compound 3 are as follows:

Melting point: 140–142° C.;

$^1$H NMR (200 MHz, DMSO $d_6$) δ: 9.76 (s, 4H), 7.19 (d, J=2.0 Hz, 4H), 7.15 (d, J=2.0 Hz, 4H), 4.96 (d, J=11.5 Hz, 2H), 4.42 (J=11.9 Hz, 2H), 4.30–3.86 (m, 28H), 3.72–3.50 (m, 28H), 3.16 (d, J=13.5 Hz, 2H), 3.09 (J=13.2 Hz, 2H), 2.98 (d, J=21.4 Hz, 8H), 1.20 (t, J=7.0 Hz, 24H);

FD-MS m/z 1338.4 (17%) [M$^+$ 1337.2], 1360.3 (100%) [M$^+$+Na 1360.2], 1376.3 (16%) [M+K].

EXAMPLE 4

In this example, the efficiency of the calixarene of example 1 (Compound 1) in the separation of the trivalent lanthanides Pm, Eu, Gd and Tb is evaluated.

For this purpose, 3 ml of an aqueous solution of 4M NaNO$_3$, 0.01 M HNO$_3$ containing approximately 10$^{-6}$ mol/l of the element to be separated (Eu, Gd, Tb) and approximately 2.10$^{-9}$ mol/l in the case of Pm is placed in contact with 3 ml of an organic solution composed of chloroform containing 10$^{-4}$ mol/l of compound 1.

The contact is carried out in a 20 ml polypropylene tube which is placed under stirring. After 1 hour of contact, the two phases are allowed to settle and the rare earth concentrations of each phase are determined by γ spectrometry or by liquid scintillation (Pm).

The distribution coefficient D, which corresponds to the ratio of the concentration of the element (rare earth) in the organic phase to the concentration of the same element in the aqueous phase is then determined. The results obtained are given in table 1.

In table 1, the results obtained with the calixarene tetra-O-pentyltetrakis(diphenyl phosphin-oxide acetamide) calix[4]arene (Compound 8 of table 1 in the document WO96/93800 [1]) when the same test is performed, but using 10$^{-3}$ mol/l of said calixarene in chloroform are given as an indication.

The results in table 1 demonstrate that the calixarene according to the invention makes it possible to obtain distribution coefficients of the same order of magnitude as those obtained with the calixarene according to the prior art, but in this case, the calixarene according to the prior art is used at a 10 times higher concentration.

EXAMPLE 5

In this example, the efficiency of the calixarene in example 2 (Compound 2) in the separation of lanthanum, cerium, neodymium, samarium, europium and americium is evaluated, using aqueous solutions containing one of these elements, the nitric acidity of the solutions varying from 10$^{-2}$ mol/l to 4 mol/l.

In this example, 3 ml of each aqueous solution containing approximately 10$^{-5}$ mol/l of the element to be separated is placed in contact with 3 ml of an organic solution composed of nitrophenylhexyl ether (NPHE) containing 10$^{-3}$ mol/l of the calixarene 2. The contact is carried out in a 20 ml polypropylene tube which is placed under stirring. After 1 hour of contact, the two phases are allowed to settle and the activity of each phase is counted by liquid scintillation or by a or y spectrometry.

The distribution coefficient D, which corresponds to the ratio of the concentration of the element (rare earth) in the organic phase to the concentration of the same element in the aqueous phase is then determined.

The results obtained are given in table 2.

COMPARATIVE EXAMPLE 1

In this example, the same procedure as in example 5 is followed to test the efficiency of a calixarene according to the prior art in the separation of europium and americium.

The results obtained are given in table 3.

If the results in tables 2 and 3 are compared, it is noted that the calixarene according to the invention is much more efficient in the extraction of europium and americium than the calixarene according to the prior art.

EXAMPLE 6

In this example, the same procedure as in example 5 is followed to test the efficiency of compound 3 in the separation of the same elements. The results obtained are given in table 4 attached.

COMPARATIVE EXAMPLE 2

In this example, the same procedure as in example 6 is followed to test the efficiency of the calixarene according to the formula:

which shows the same structure as compound 3, but without the ether-ring links.

Under these conditions, for $HNO_3$ concentrations ranging from $10^{-2}$ M to 4M, distribution coefficients D that are always less than 0.1 are obtained, which indeed demonstrates the improved efficiency of the calixarene according to the invention due to the presence of the ether-ring links.

COMPARATIVE EXAMPLE 3

In this example, the same procedure as in example 5 is followed, but CMPO at a concentration of 0.25 mol/l in nitrophenyl hexyl ether is used as an organic liquid phase to separate the same elements. The formula of CMPO is as follows:

(iBu = isobutyl)

The results obtained are given in table 5.

If the results in table 5 are compared to those in table 2 for calixarene 2, it is noted that the use of CMPO requires much higher concentrations (0.25 mol/l instead of $10^{-3}$ mol/l) to obtain results of the same order of magnitude.

Therefore, the calixarenes according to the invention are much more beneficial.

REFERENCES

[1]: WO-A-96/23800.
[2]: FR-A-2 698 362.
[3]: A. Arduini et al in J. Org. Chem., 1995, 100, p. 1454–1457 [3].
[4]: Arduini et al, Tétrahédron, 1996, 52, p. 6011–6018.

TABLE 1

DISTRIBUTION COEFFICIENTS

| Organic phase | Pm | Eu | Gd | Tb |
|---|---|---|---|---|
| Calixarene 1 ($10^{-4}$M) in $CHCl_3$ | 14.6 | 4.7 | 2.7 | 1.5 |
| Calixarene according to the prior art ($10^{-3}$M) in $CHCl_3$ | 15.2 | 5.2 | 2.4 | 0.8 |

TABLE 2

DISTRIBUTION COEFFICIENTS
Compound 2 ($10^{-3}$M) in NPHE

| $HNO_3$ | $10^{-2}$M | $10^{-1}$M | 1M | 1.5M | 2M | 3M | 4M |
|---|---|---|---|---|---|---|---|
| La | 2.35 | 75 | 180 | 160 | 215 | 190 | 115 |
| Ce | 1.8 | 60 | 13.5 | 12 | 14 | 14 | 12 |
| Nd | 0.6 | 21 | 165 | 190 | 260 | 205 | 90 |
| Sm | 0.14 | 5.2 | 65 | 100 | 135 | 95 | 37 |
| Eu | 0.12 | 2.2 | 30 | 45 | 60 | 50 | 18 |
| Am | 0.73 | 25 | 250 | 370 | 405 | 305 | 115 |
| Cm | 0.31 | 8.7 | 77 | 75 | 78 | 95 | 200 |

TABLE 3

DISTRIBUTION COEFFICIENTS
Calixarene according to the formula ($10^{-3}$ M) in NPHE

| $HNO_3$ | $10^{-2}$M | $10^{-1}$M | 1M | 1.5M | 2M | 3M | 4M |
|---|---|---|---|---|---|---|---|
| Eu | 0.02 | 0.06 | 1.8 | 3.7 | 1.6 | 6 | 3 |
| Am | 0.07 | 0.45 | 12 | 15 | 9 | 40 | 22 |

TABLE 4

DISTRIBUTION COEFFICIENTS
Compound 3 ($10^{-3}$M) in NPHE

| HNO$_3$ | $10^{-2}$M | $10^{-1}$M | 1M | 1.5M | 2M | 3M | 4M |
|---|---|---|---|---|---|---|---|
| La | 0.28 | 0.41 | 2.25 | 3.7 | 5.05 | 5.55 | 5 |
| Ce | 0.28 | 0.42 | 2.2 | 3.6 | 4.8 | 5.3 | 5.1 |
| Nd | 0.29 | 0.32 | 1.15 | 1.85 | 2.65 | 3.15 | 3.25 |
| Sm | 0.27 | 0.28 | 0.48 | 0.85 | 1.4 | 1.65 | 2.25 |
| Eu | 0.27 | 0.28 | 0.29 | 0.56 | 1 | 1.25 | 1.75 |
| Am | 0.22 | 0.25 | 1.1 | 2.05 | 2.7 | 3.1 | 3.5 |

TABLE 5

DISTRIBUTION COEFFICIENTS
CMPO (0.25M) in NPHE

| HNO$_3$ | $10^{-2}$M | $10^{-1}$M | 1M | 1.5M | 2M | 3M | 4M |
|---|---|---|---|---|---|---|---|
| La | 0.92 | 12.9 | 67 | 62 | 70 | 51 | 38 |
| Ce | 1.6 | 21 | 14 | 12.5 | 13 | 12.5 | 11.5 |
| Nd | 1.7 | 23 | 125 | 115 | 135 | 100 | 75 |
| Sm | 1.6 | 21 | 140 | 130 | 160 | 110 | 90 |
| Eu | 1.2 | 16 | 110 | 105 | 125 | 90 | 75 |
| Am | 2.5 | 35 | 200 | 155 | 195 | 150 | 105 |
| Cm | 1.7 | 26 | 90 | 95 | 52 | 50 | 68 |

What is claimed is:

1. Calixarene according to the formula:

wherein $R^1$ and $R^2$ which may be identical or different, are alkyl, alkoxy or aryl groups, and n is an integer equal to 2, 3 or 4.

2. Calixarene according to claim 1, wherein n is equal to 2.

3. Calixarene according to claim 1, wherein $R^1$ and $R^2$ represent a phenyl group.

4. Calixarene according to claim 1, wherein $R^1$ and $R^2$ represent an ethoxy group.

5. Calixarene according to claim 1, wherein $R^1$ represents an ethoxy group and $R^2$ represents a phenyl group.

6. A method to prepare a calixarene of formula (I):

wherein $R^1$ and $R^2$, which may be identical or different, are alkyl, alkoxy or aryl groups, and n is an integer equal to 2, 3 or 4, comprising the following steps:

a) nitrating a calixarene of formula (II):

wherein $R^3$ represents an alkyl group and n is as defined above, to obtain the nitro compound of formula (III):

b) reducing the nitro compound of formula (III) into an amino compound of formula (IV):

(IV)

c) reacting the amino compound of formula IV with a phosphinoxide acetate of formula (V):

(V)

wherein $R^1$ and $R^2$ are as defined above, and $R^4$ represents a p-nitrophenyl or 2,4 dinitrophenyl group.

7. Method to prepare a calixarene according to the formula:

(I)

wherein $R^1$ is an alkyl, alkoxy or aryl group, $R^2$ is an alkoxy group, and n is an integer equal to 2, 3 or 4, comprising the following steps:

a) nitrating a calixarene of formula (II):

(II)

wherein $R^3$ represents an alkyl group and n is as defined above, to obtain the nitro compound of formula (III):

(III)

b) reducing the nitro compound of formula (III) into an amino compound of formula (IV):

(IV)

c) reducting the amino compound of formula (IV) with bromoactyl chloride of formula (VI):

BrCH$_2$COCl  (VI)

to obtain the calixarene of formula (VII):

(VII)

d) reacting the compound of formula (VII) with a phosphonate or phosphinate of formula (VIII):

R$^1$—P—(R$^2$)$_2$  (VIII)

wherein R$^1$ is an alkyl, alkoxy or aryl group and R$^2$ is an alkoxy group.

8. A method to separate at least one metal selected from actinides and lanthanides present in an aqueous solution, which includes placing the aqueous solution in contact with a non-miscible phase comprising at least one calixarene of formula (I):

(I)

wherein R$^1$ and R$^2$ which may be identical or different, are alkyl, alkoxy or aryl groups, and n is an integer equal to 2, 3 or 4, to extract the metal(s) in the non-miscible phase.

9. Method according to claim 8, wherein the aqueous solution is a nitric solution containing 1 to 4 mol/l of HNO$_3$.

10. Method according to claim 8, wherein the non-miscible phase is a solution of calixarene(s) according to formula (I) in an organic solvent.

11. Method according to claim 10, wherein the organic solvent is a nitrophenyl alkyl ether.

12. Calixarene according to claim 2, wherein R$^1$ and R$^2$ represent a phenyl group.

13. Calixarene according to claim 2, wherein R$^1$ and R$^2$ represent an ethoxy group.

14. Calixarene according to claim 2, wherein R$^1$ represents an ethoxy group and R$^2$ represents a phenyl group.

* * * * *

UNITED STATES PATENT AND TRADEMARK OFFICE
CERTIFICATE OF CORRECTION

PATENT NO.    : 6,630,114 B1                                    Page 1 of 1
DATED         : October 7, 2003
INVENTOR(S)   : Dozol et al.

It is certified that error appears in the above-identified patent and that said Letters Patent is hereby corrected as shown below:

<u>Title page, Item [54] and Column 1, lines 1-4,</u>
Title should read:
-- CALIXARENE DERIVATIVES, PREPARATION METHOD AND USE OF SAID DERIVATIVES TO EXTRACT ACTINIDES AND LANTHANIDES --

Signed and Sealed this

Thirtieth Day of December, 2003

JAMES E. ROGAN
*Director of the United States Patent and Trademark Office*